US010683525B2

(12) United States Patent
Luley et al.

(10) Patent No.: US 10,683,525 B2
(45) Date of Patent: Jun. 16, 2020

(54) METHOD FOR PRODUCING 2-O-GLYCERYL-ALPHA-D-GLUCOPYRANOSIDE (71) Applicant: Technische Universität Graz, Graz (AT)

(72) Inventors: Christiane Luley, Graz (AT); Thornthan Sawangwan, Bangkok (TH); Bernd Nidetzky, Graz (AT); Mario Müller, Graz (AT)

(73) Assignee: TECHNISCHE UNIVERSITÄT GRAZ, Graz (AT)

(*) Notice: Subject to any disclaimer, the term of this patent is extended or adjusted under 35 U.S.C. 154(b) by 2 days.

(21) Appl. No.: 15/985,777

(22) Filed: May 22, 2018

(65) Prior Publication Data
US 2018/0265907 A1    Sep. 20, 2018

Related U.S. Application Data (62) Division of application No. 12/442,288, filed as application No. PCT/AT2007/000448 on Sep. 21, 2007, now abandoned.

(30) Foreign Application Priority Data

Sep. 21, 2006  (AT) ................................ 1577/2006

(51) Int. Cl.
C12P 19/44    (2006.01)
A23L 27/30    (2016.01)
A61K 8/60     (2006.01)
A61K 31/7032  (2006.01)
A61Q 19/00    (2006.01)
A61Q 19/10    (2006.01)

(52) U.S. Cl.
CPC ............ C12P 19/44 (2013.01); A23L 27/33 (2016.08); A61K 8/602 (2013.01); A61K 31/7032 (2013.01); A61Q 19/00 (2013.01); A61Q 19/10 (2013.01)

(58) Field of Classification Search
None
See application file for complete search history.

(56) References Cited

U.S. PATENT DOCUMENTS 4,511,694 A     4/1985  Kramer et al.
5,891,854 A *   4/1999  Thiem .................. A61K 8/60
                                                514/25

FOREIGN PATENT DOCUMENTS

| JP | 05-091891 A | 4/1993 | |
| JP | H05-91891 * | 5/1993 | ............ C12P 19/18 |
| JP | 2004-331578 A | 11/2004 | |
| JP | 2004-331579 A | 11/2004 | |
| JP | 2004-331580 A | 11/2004 | |
| JP | 2004-331582 A | 11/2004 | |
| JP | 2004-331583 A | 11/2004 | |
| WO | 2004/101744 A2 | 11/2004 | |

OTHER PUBLICATIONS

Hincha et al., "Stabilization of model membranes during drying by compatible solutes involved in the stress tolerance of plants and microorganisms" Biochem. J. (2004) 383, 277-283 (Year: 2004).*
English machine translation of Japanese patent H05-91891, downloaded from translationportal.epo.org (Year: 1993).*
Borges et al., "Comparative study of the thermostabilizing properties of mannosylglycerate and other compatible solutes on model enzymes" Extremophiles vol. 6 pp. 209-216 (Year: 2002).*
Takenaka et al., "Effects of alpha-D-Glucosylglycerol on the in vitro Digestion of Disaccharides by Rat Intestinal Enzymes" Biosci Biotechnol Biochem vol. 65 No. 7 pp. 1458-1463 (Year: 2001).*
Fujita et al., "Long-Term Ingestion of a Fermented Soybean-Derived Touchi-Extract with a-Glucosidase Inhibitory Activity Is Safe and Effective in Humans with Borderline and Mild Type-2 Diabetes" Journal of Nutrition vol. 131 pp. 2105-2108 (Year: 2001).*
CAS Registry No. 22160-26-5, accessed on Apr. 9, 2009, https://scifinder.cas.org.
Coutinho, P. M., et al., "An Evolving Hierarchical Family Classification for Glycosyltransferases," J. Mol. Biol. (2003), 328:307-317.
Enzyme Database—BRENDA—Sucrose phosphorylas from Leuconostoc mesenteroides: EC 2.4.1.7, Jul. 2011.
Goedl, C. et al. "A High-Yielding Biocatalytic Process for the Production of 2-O-(a-D-glucopyranosyl)-sn-glycerol, a Natural Osmolyte and Useful Moisturizing Ingredient" Angew. Chem. Int. Ed. 2008, 47, 1008-10089.
Guibert, A., et al., "Part V. Biocatalytic Production of Chemicals: Production and Purification of Sucrose Phosphorylase from Leuconostoc mesen teroides," Annals New York Academy of Sciences, (2006), 542:307-311.
JP 2009-528546 Office Action dated Mar. 19, 2013.
Kaushal, G. P., et al., "Plant Glucosidase II Catalyzes a Transglucosylation Reaction in Addition to the Hydrolytic Reaction," Archives of Biochemistry and Biophysics (1989), 272:481-487.
Kawasaki, H., et al., "Cloning and Expression in *Escherichia coli* of Sucrose Phosphorylase Gene from Leuconostoc mesenteroides No. 165," Biosci Biotech Biochem (1996), 60:322-324.
Kitao, S. et al. "Transglucosylation Catalyzed by Sucrose Phosphorylase from Leuconostoc mesenteroides and Production of Glucosyl-xylitol" Biosei. Biotech. Biochem., 56 (12), 2011--2014, 1992.

(Continued)

Primary Examiner — Eric Olson
(74) Attorney, Agent, or Firm — Edwin S. Flores; Daniel J. Chalker; Chalker Flores, LLP (57) ABSTRACT The present invention relates to a method for producing 2-O-glyceryl-α-D-glucopyranoside (αGG; FIG. 1) from a glucosyl donor and a glucosyl acceptor comprising the steps: providing a sucrose phosphorylase (EC 2.4.1.7), incubating said sucrose phosphorylase with a mixture comprising a glucosyl donor and glycerol as glucosyl acceptor and isolating and/or purifying 2-O-glyceryl-α-D-glucopyranoside.

21 Claims, 3 Drawing Sheets (56) References Cited

OTHER PUBLICATIONS

Kitao, S., et al., "Cloning of the Sucrose Phosphorylase Gene from Leuconostoc mesenteroides and Its Overexpression Using a 'Sleeper' Bacteriophage Vector," Journal of Fermentation and Bioengineering (1992), 73:179-184.

Marin, K., et al., "The ggpS Gene from *Synechocystis* sp. Strain PCC 6803 Encoding Glucosyl-Glycerol-Phosphate Synthase Is Involved in Osmolyte Synthesis," Journal of Bacteriology (1998), 180:4843-4849.

Mieyal, J. et al. "Mechanism of Action of Sucrose Phosphorylase" The Journal of Biological Chemistry vol. 247, No. 2, Issue of Jan. 25, pp. 532-542, 1972.

Nakano, H., et al., "Synthesis of Glucosyl Glycerol by Cyclodextrin Glucanotransferases," Journal of Bioscience and Bioengineering (2003), 95:583-588.

Pimentel, M.C.B., et ,al. "Immobilized Sucrose Phosphorylase from Leuconostoc mesenteroides," Appl Biochem Biotechnol (1991), 27:37-43.

Roder, A., et al., "Synthesis of the compatible solutes glucosylglycerol and trehalose by salt-stressed cells of Stenotrophomonas strains," FEMS Microbiology Letters (2005), 243:219-226.

Slatner, M., et al., "Kinetic Study of the Catalytic Mechanism of Mannitol Dehydrogenase from Pseudomonas fluorescens," Biochemistry (1999), 38:10489-10498.

Takenaka, F., et al., "Identification of α-D-Glucosylglycerol in Sake," Biosci Biotechnol Biochem (2000), 64:378-385.

Takenaka, F., et al., "Synthesis of α-D-Glucosylglycerol by α-Glucosidase and Some of Its Characteristics," Biosci Biotechnol Biochem (2000), 64:1821-1826.

Trincone, A., et al., "Enzymatic Synthesis of Carbohydrate Derivatives using β-Glycosidate of Sulfolobus solfataricus," Biocatalysis (1994), 10:195-210.

Van Den Broek, L.A.M., et al., "Physico-chemical and transglucosylation properties of recombinant sucrose phosphorylase from Bifidobacterium adolescentis DSM20083," Appl Microbiol Biotechnol (2004), 65:219-227.

Vandamme, E J., et al., "Microbial Sucrose Phosphorylase: Fermentation Process, Properties and Biotechnical Applications," Advances in Applied Microbiology (1987) pp. 163-201.

Yamamoto, T., et al., "Acceptor Recognition of Kojibiose Phosphorylase from Thermoanaerobacter brockii: Synthesis of Glycosyl Glycerol and myo-Inositol," Journal of Bioscience and Bioengineering (2006), 101:427-433.

* cited by examiner

METHOD FOR PRODUCING 2-O-GLYCERYL-ALPHA-D-GLUCOPYRANOSIDE

CROSS-REFERENCE TO RELATED APPLICATIONS

This patent application is a divisional application of U.S. patent application Ser. No. 12/442,288 filed on Mar. 20, 2009 and which claims priority to International Application No. PCT/AT2007/000448 filed Sep. 21, 2007, which claims the priority of A 1577/2006, filed on Sep. 21, 2006. The contents of which is incorporated by reference in its entirety.

TECHNICAL FIELD OF THE INVENTION

The present invention relates to methods for producing α-D-glucosylglycerol (2-O-glyceryl-α-D-glucopyranoside).

Simple and complex carbohydrates govern a diverse range of cellular functions, including energy storage, cell-wall structure, cell-cell interaction and signalling, host-pathogen interactions and protein glycosylation. They also serve a function as osmolytes and small molecules of extreme lifestyles. Glycosyltransferases (GTs) are the enzymes responsible for the synthesis of glycosides in nature whereas, glycosylhydrolases (GHs) have been evolved to degrade them. Among GT and GH classes, the glycoside phosphorylases (GPs) are special in several respects. GPs catalyze the phosphorolysis of α- and β-D-glycosides, mainly glucosides (Glc-OR) including disaccharides and oligo- or polysaccharides of varying degree of polymerisation. Glucosyl transfer to phosphate (Pi) is favoured thermodynamically in vivo because phosphate is usually present in large excess over α-D-glucose 1-phosphate (Glc 1-P). However, thermodynamic equilibrium constants ($K_{eq}$) of GP-catalysed reactions are intermediate of $K_{eq}$ values for the reaction of GTs ($K_{eq} \ll 1$) and GHs ($K_{eq} \gg 1$). The relatively favourable $K_{eq}$ values and the fact that phospho-activated sugars are less expensive than nucleotide-activated ones, which are required by most GTs, make GPs interesting biocatalysts for the stereo- and regio-specific synthesis of glucosides.

Increased attention has recently been directed towards novel α-D-glucosides, in particular α-D-glucosylglycerol (2-O-glyceryl-α-D-glucopyranoside; αGG) for which several applications are presently being developed. αGG functions as a compatible solute in microorganisms, providing some protection against stresses due to high salt concentrations, heat, and UV-radiation. αGG is purportedly useful as an alternative sweetener in food stuffs because of its low cariogenicity and caloric value in comparison to sucrose. Furthermore, αGG and derivates thereof are studied as therapeutics in diseases caused by protein misfolding and in cancer therapy. In cosmetics, αGG may be used as an anti-aging agent and moisture-regulating compound.

αGG can be produced by chemical as well as by enzymatic methods. Chemical methods may involve various start compounds like maltitol, isomaltose, trehalulose etc. (see e.g. Takenaka F. et al. Biosci. Biotechnol. Biochem. (2000) 64:378-385). Enzymes which catalyze the synthesis of αGG may involve α-glucosidase (Takenaka F. and Uchiyama H. Biosci. Biotechnol. Biochem. (2000) 64:1821-1826), cyclo-dextrin glucanotransferase (Nakano H. et al. J. Biosci. Bioeng. (2003) 95:583-588), glucosyl-glycerol-phosphate synthase (Marin K. et al. J. Bacteriol. (1998) 180:4843-4849) and plant glucosidase II (Kaushal G P et al. Arch. Biochem. Biophys. (1989) 272:481-487). All current procedures for the synthesis of αGG exhibit one or more of the following crucial disadvantages: multiple steps of reaction (including activation, protection and deprotection); labor-intensive synthesis and work-up; low yield and productivity; low atom economy; long reaction times. Consequently, no industrial process for production of αGG has been developed and the product is not available on the market.

The chemical synthesis of stereochemical pure natural αGG is technically not feasible due to extremely laborious procedures and low yield. Microbial synthesis of αGG has been shown but the productivity is poor. Enzymatic synthesis of αGG using transglucosylation by aglucosidases is a possibility which has been described but the main drawback of the process is the wrong regioselectivity of the known enzymes which prefer the primary rather than the secondary hydroxy group of glycerol. The product mixture synthesized by α-glucosidases contains only 30% of the correct natural αGG, requiring a substantial effort in the product isolation.

The microbial synthesis of αGG is presently not a mature process, especially when the yield of αGG is taken into account, because it does not allow to produce αGG as a bulk chemical. The attainable product concentrations are very low (e.g. 29 mg/l; Roder et al. FEMS Microbiol. Lett. (2005) 243: 219-226) and also the productivity (≥3 days of production) is not advantageous for the industrial production.

JP 2001/245690 A relates to a method for producing glycosides and oligosaccharides by using a glucosidase, in particular β-galactosidase.

It is an object of the present invention to provide an enzymatic method for the production of stereochemical pure αGG in high yield overcoming the drawbacks of the methods known in the art. Furthermore the method should preferably allow the use of economic substrates.

BRIEF DESCRIPTION OF THE SEVERAL VIEWS OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
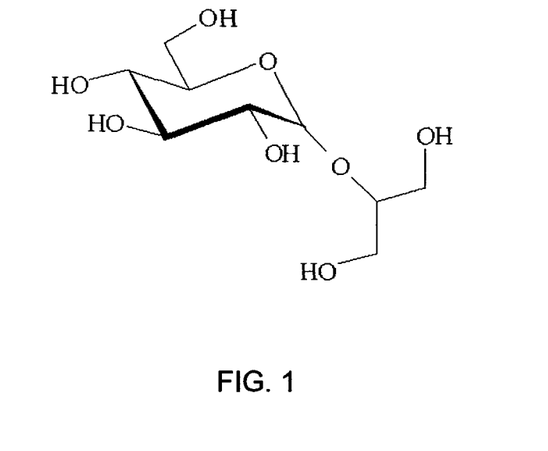
FIG. 1 is an image that shows the chemical structure of αGG.

Therefore, the present invention relates to a method for producing 2-O-glyceryl-α-D-glucopyranoside (αGG; FIG. 1) from a glucosyl donor and a glucosyl acceptor comprising the steps:

providing a sucrose phosphorylase (EC 2.4.1.7),
incubating said sucrose phosphorylase with a mixture comprising a glucosyl donor and glycerol as glucosyl acceptor and isolating and/or purifying 2-O-glyceryl-α-D-glucopyranoside.

Sucrose phosphorylase (SPase; EC 2.4.1.7) catalyzes the conversion of sucrose and phosphate into D-fructose and Glc 1-P. SPase has been isolated from a number of bacterial sources. Genes encoding SPase have been cloned from different bacteria and expressed heterologously (Kawasaki H et al., Biosci. Biotech. Biochem. (1996) 60:322-324; Kitao S and Nakano E, J. Ferment. Bioeng. (1992) 73:179-184; van den Broek L A M et al., Appl. Microbiol. Biotechnol. (2004) 65:219-227). According to the systematic sequence-based classification of glycosylhydrolases (GH) and glycosyltransferases (GT) (Coutinho P M et al. J. Mol. Biol. (2003) 328:307-317; Henrissat B. Biochem. J. (1999) 280:309-316) SPase belongs to family GH13 (Clan GH-H), often referred to as the α-amylase family. The three-dimensional structure of SPase from *Bifidobacterium adolescentis* has been solved recently, revealing an (β/α)8 barrel fold and a catalytic site in which two carboxylate groups probably fulfill the role of a nucleophile (Asp192) and a general acid/base (Glu232).

The reaction of SPase proceeds with net retention of the anomeric configuration and occurs through a double displacement mechanism involving two configurationally inverting steps: cleavage of the carbon-oxygen bond of the glucosyl donor and formation of a covalent β-glucosyl-enzyme (β-Glc-E) intermediate; and reaction of the intermediate with phosphate to yield Glc 1-P. In a side reaction, the β-Glc-E intermediate may be intercepted by water, leading to hydrolysis. Hydrolytic conversion of sucrose is irreversible but proceeds nearly two orders of magnitude slower than the phosphorolytic reaction. SPase also catalyzes transglucosylation reactions which occur in competition with hydrolysis and whereby the β-Glc-E intermediate is attacked by external nucleophiles and new α-D-glucosides are produced.

Biochemical studies have shown that SPase is strictly specific for transferring a glucosyl moiety and does not tolerate structural modifications on the glucopyranosyl ring including epimerisation and deoxygenation. The list of known glucosyl donors for SPase is therefore short: sucrose, Glc 1-P and α-D-glucose 1-fluoride. By contrast, the specificity of SPase for glucosyl acceptors is comparably relaxed.

The selectivity of SPase which forms only natural αGG in a high quantitative yield (>95%) are crucial points of the method according to the present invention. The method of the present invention may use very cheap substrates (which are both available from large-scale industrial processing) without any chemical derivatisation (required in chemical synthesis) and is characterized by an extremely high atom efficiency because all substrate converted goes quantitatively into product. During microbial fermentation, for example, most of the substrate is used for growth and maintenance energy and only a small part of it is used for αGG production. In the method of the present invention only one enzyme is required and this may be of natural or recombinant preparation, used as free or immobilized, as isolated enzyme or in another catalyst form (permeabilized or resting cells).

The method of the present invention is preferably performed in vitro with purified enzyme or an enzyme extract, whereby the SPase employed may be obtained from at least one source, which means that also SPases of more than one type (origin) may be employed.

Synthesis of αGG is preferably performed using a protein concentration of sucrose phosphorylase delivering an activity of between 1,000 and 1,000,000 units/litre (one unit is defined as the enzyme activity that converts 1 μmol of substrate per min under standard reaction conditions, typically 30° C., reported in the literature.)

"Sucrose phosphorylase" as used herein refers not only to enzymes of the EC 2.4.1.7 class but also to molecules which exhibit the same properties in relation to its substrates and products. Such molecules include also fusion proteins of sucrose phosphorylase with other peptides, polypeptides or proteins, which exhibit potentially also enzymatic or binding activities.

According to a preferred embodiment of the present invention the glucosyl donor is selected from the group consisting of sucrose and analogues of sucrose in which the fructosyl moiety has been modified or substituted by another ketosyl residue, Glc 1-P, α-D-glucose-1-fluoride, further stable, activated glucosyl donors such as α-D-glucose-1-azide, and mixtures thereof.

The glucosyl donor to be employed in the method of the present invention can be any one which serves as substrate for the transglycosylation reaction catalysed by the SPase.

The use of sucrose (a disaccharide consisting of glucose and fructose) in the method of the present invention will lead not only to the formation of αGG but also to the formation of fructose. If substrates like Glc 1-P or α-D-glucose-1-fluoride are employed, phosphate or fluoride will be products formed in addition to αGG. The achievable yield will depend on the energy content of the glucosyl donor and is greater than 30%, preferably greater than 50%, and in particular greater than 90%.

The sucrose phosphorylase used in a method according to the present invention is preferably of microbial, preferably bacterial origin.

The advantage of using microbial SPases is the simple production and isolation and stability of these enzymes. They can be obtained from microorganisms naturally or recombinantly expressing SPase.

According to a preferred embodiment of the present invention the bacterial sucrose phosphorylase is obtained from *Agrobacterium vitis* (NCBI P33910), *Bifidobacterium adolescentis* (Q84HQ2), *Bifidobacterium longum* (Q84BY1), *Escherichia coli* (P76041), *Escherichia coli* 06 (Q8FHS2), *Lactobacillus acidophilus* (Q7WWP8, Q7WWQ5), *Lactobacillus delbrueckii* subsp. *lactis* (Q71I99), *Leuconostoc mesenteroides* (Q59495, Q9R5Q3), *Listeria monocytogenes* (Q4ENE7, Q4EQR2, Q4ETN7, Q4EHA0, Q4EJW2, Q4ELY7), *Pseudomonas putrefaciens, Pseudomonas saccharophila* (AAD40317), *Rhodopirellula baltica* (Q7UIS9), *Shewanella baltica* (Q3Q4P1), *Shewanella frigidimarina* (Q3NMD1), *Solibacter usitatus* (Q43TL5), *Streptococcus mutans* (P10249) and/or *Synechococcus* sp. (068858, Q7U3J7).

It is particularly preferred to use at least one SPase derived from *Leuconostoc mesenteroides*.

The SPase is preferably recombinantly produced as a full-length protein or a catalytically active fragment thereof or a fusion protein. However, it is of course also possible to use SPase directly from the organism which naturally produces said SPase. Methods for the recombinant production of SPase are known to the person skilled in the art (e.g. Sambrook J. et al. Molecular cloning: a laboratory manual. ISBN 0-87969-309-6).

As used herein, "full-length protein" refers to SPase encoded by a gene derived from an organism as, for instance, listed above. Said naturally occurring gene, in particular the SPase encoding region of said gene, is directly employed for the recombinant production of SPase.

"A catalytically active fragment" of SPase refers to protein fragments of SPase which have the same or substantially the same activity and substrate specificity as native SPase. The length of the fragments is not crucial provided that the fragments will have the same or similar substrate specificity and catalyse the formation of the same products as native SPase.

As used herein, "a fusion protein" refers to SPase or catalytically active fragments thereof recombinantly fused to at least one further protein, polypeptide or peptide. Said at least one further protein, polypeptide or peptide may be of any kind (e.g. enzyme).

It is noted that within the scope of the invention also variants (i.e. mutations including deletions, substitutions and insertions) of SPase are summarised, provided that these variants have the same or substantially the same (e.g. increased catalytical activity) activity as native SPase.

According to the present invention the SPase may be employed in the incubation step as either a cell-free enzyme, which may but need not be partially purified, a whole-cell system pretreated physically or chemically for improved permeability of the cell membrane (permeabilisation) and mechanical stability, encapsulated catalyst in which said free enzyme or whole-cell system are entrapped, preferably in gel-like structures, or immobilized on a carrier. A recent comprehensive summary of methods of enzyme immobilisation, including the permeabilisation of cells is given by Cao L., Carrier-bound Immobilized Enzymes (2005) Wiley-VCH, Weinheim.

Advantageously the SPase is immobilised on a carrier which preferably is a solid support. Any material that binds said SPase noncovalently, preferably natural or nonnatural polymers with anion exchange properties, or covalently, preferably a polymer, more preferably an acrylic polymer, in particular a copolymer of methacrylamide, N,N'-methylen-bis(acrylamide) and a monomer carrying oxirane groups.

The carrier is preferably a chromatography resin, preferably selected from the group consisting of anion exchange chromatography resin, cation exchange chromatography resin, affinity chromatography resin (e.g. comprising immobilised SPase specific antibodies) and hydrophobic interaction chromatography resin.

The SPase of the present invention may be immobilised (temporarily or covalently) on any carrier, preferably particles (e.g. beads), in particular chromatography resin, provided that the enzymatic activity of the enzyme is not affected in a way to change its substrate specificity or to reduce its activity to low conversion rates.

The carrier may comprise functional groups which require—in order to bind the SPase on the resin—that also the enzyme carries corresponding binding partners (e.g. streptavidin—biotin, chelated metal ions—$His_6$-tag).

To improve the affinity of the enzyme to carriers lacking said functional groups, SPase may be recombinantly produced as a fusion protein harboring a binding peptide, preferably one showing ion-exchange properties, or a binding domain, preferably a polysaccharide binding domain, in particular a cellulose binding domain.

Several advantages are offered by the use of insoluble immobilized enzymes (carrier-bound, encapsulated, whole-cell systems) in the method of the present invention:

1. the immobilized enzyme is easily recovered from the reaction mixture at the conclusion of the reaction for reuse, whereas the soluble enzyme is only recovered with difficulty and loss of activity;
2. the immobilized enzyme is more stable than the soluble enzyme, both for the number of enzyme turnovers obtained versus the soluble enzyme, as well as for recovered enzyme activity at the conclusion of a reaction or after prolonged storage in aqueous buffer.

No specific method of immobilization can be chosen for a particular enzyme with the expectation that the immobilization will be successful. Furthermore, the expectation for successful co-immobilization of more than one enzyme is even less predictable. It is generally agreed by those skilled in the art that a successful immobilization of any enzyme must be discovered by screening a variety of methods, and an optimal result obtained by trial and error. The immobilization of SPase on a carrier stabilizes the enzyme activity. Literature shows that entrapment of the enzyme also improves the stability (Soetaert W. et al., Progress in Biotechnology Vol. 10 (Petersen S. B., Svensson, B., Pederesen, S., Eds), Elsevier, Amsterdam). The immobilization of enzymes can be performed using a variety of techniques, including: (1) binding of the enzyme to a carrier or support, via covalent attachment, physical adsorption, electrostatic binding, or affinity binding, (2) crosslinking with bifunctional or multifunctional reagents, (3) entrapment in gel matrices, polymers, emulsions, or some form of membrane, and (4) a combination of any of these methods. Detailed descriptions of many of these methods of enzyme immobilization, and the various factors affecting the choice of a method of immobilization, are collected in the following volumes of Methods in Enzymology, K. Mosbach (ed.), Academic Press, New York: Vol. 44 (1976), Vol. 135 (1987), Vol. 136 (1987), Vol. 137 (1988), and the references therein.

The immobilization of SPase on oxirane acrylic beads Eupergit C and Eupergit C-250L (Rohm Pharma) resulted in a catalyst (enzyme+carrier) which was particularly stable to the reaction conditions and had a sufficiently high specific activity (units of enzyme activity/gram of catalyst). However, to be useful in the method of the present invention, both free and immobilized preparations of SPase can be used.

However, many of the deficiencies of the soluble enzymes can be eliminated by employing the immobilized enzyme catalyst. The stability of immobilized SPase in aqueous buffers is much greater than the soluble enzyme. Recovery and reuse of the immobilized catalyst was easily performed by simply filtering the catalyst away from the reaction mixture and recycling it to fresh reaction mixture; in this manner for immobilized SPase a high number of turnovers (i.e., the number of substrate molecules that are converted to product molecules per catalyst molecule before inactivation of the enzyme) can be achieved.

The immobilized SPase used in the reaction should be present in an effective concentration, usually a concentration of about 0.001 to about 100.0 IU/ml, preferably about 10 to about 50 IU/ml. An IU (International Unit) is defined as the amount of enzyme that will catalyze the transformation of one micromole of substrate per minute.

Upon completion of the reaction the SPase bound to a carrier may be removed by filtration or centrifugation. If the immobilized SPase is packed in a column (e.g. chromatographic column) the production of αGG can be achieved in a continuous way without the necessity of removing the immobilized SPase from the reaction mixture.

According to a preferred embodiment of the present invention the incubation of the SPase with the substrates is performed at a pH value of 4 to 10, preferably of 5 to 9, more preferably of 6 to 8, in particular of 7.

The pH value in the method according to the present invention is preferably selected from the ranges identified above, which allows an efficient conversion of the substrates into αGG.

According to another preferred embodiment of the present invention the incubation is performed for at least 15 min, preferably for at least 60 min, more preferably for at least 3 hours, even more preferably for at least 5 hours.

The incubation of the substrates with the immobilised or unbound SPase may be performed for at least 15 minutes. However it is especially preferred to select the incubation time between 1 and 48 or between 5 and 24 hours. The incubation time depends also on the incubation temperature chosen. This means if the incubation temperature is below the optimal temperature of the enzyme the incubation time may be extended.

According to a preferred embodiment of the present invention the incubation is performed at a temperature range of 10 to 50° C., preferably of 15 to 40° C., more preferably at a temperature of 30° C.

The mixture which according to the present invention is incubated with the SPase comprises the glucosyl donor, in particular sucrose, in a concentration of 0.01 to 3 mol/l, preferably of 0.05 to 2 mol/l, more preferably of 0.1 to 1.5 mol/l.

It turned out that the activity of the SPase and its substrate turnover leading to αGG is optimal in the glucosyl donor concentrations disclosed herein.

According to a preferred embodiment of the present invention the substrate mixture comprises glycerol in a concentration of 0.01 to 10 mol/l, preferably of 0.05 to 5 mol/l, more preferably of 0.1 to 3 mol/l, even more preferably of 0.1 to 1.5 mol/l.

The ratio of glycerol to glucosyl donor in the mixture ranges preferably from 0.1:1 to 10:1, preferably from 0.5:1 to 5:1, more preferably from 1:1 to 3:1.

The αGG α-D-glucosylglycerol obtainable by the method according to the present invention can be isolated by different chromatographic methods, preferably by elution chromatography on activated charcoal combined with celite as a filter aid. The product mixture obtainable by the method according to the present invention is loaded on a column of said material equilibrated in water, and elution of bound αGG is achieved with 2% ethanol. Fractions containing αGG are free of residual glycerol and product resulting from cleavage of glucosyl donor. The αGG is obtained in a yield of greater 70%, preferably greater 80%, in particular greater 90%. The purity of the product after chromatography is greater 80%, preferably greater 90%, in particular greater 95%. Following concentration under reduced pressure, solid αGG is preferably obtained by drying, preferably by lyophilisation.

Charcoal may preferably be used as suspension or more preferably packed in a column (e.g. chromatographic column). The reaction mixture potentially comprising the enzyme or residual enzyme and substrate is contacted with the charcoal (e.g. applied on a charcoal column) and successively eluted. This eluate or even the reaction mixture itself can be (further) purified using an ion exchange resin, for instance.

According to another preferred embodiment of the present invention the sucrose phosphorylase is obtained from *Leuconostoc mesenteroides* (Q59495, Q9R5Q3) and used as free or preferably immobilised enzyme preparation, preferably immobilised on an acrylic polymer, in particular a copolymer of methacrylamide, N,N'-methylen-bis (acrylamide) and a polymer carrying oxirane groups, wherein the immobilised sucrose phosphorylase is incubated with sucrose as glucosyl donor.

In particular an SPase derived from *Leuconostoc mesenteroides* immobilised on polymer particles (or gels) carrying oxirane groups was exceptionally stable and well suited for continuous reactions, for example.

Another aspect of the present invention relates to α-D-glucosylglycerol (αGG) or a product comprising α-D-glucosylglycerol (αGG) obtainable by a method according to the present invention.

The αGG or the product comprising αGG, which may be obtained by the method of the present invention, comprises the natural occurring αGG (2-O-glyceryl-α-D-glucopyranoside) in high amounts because SPase is able to specifically catalyze the formation of said αGG without significant formation of by-products resulting from transglucosylation. It is therefore of particular importance that no regioisomer mixture is contained in addition to the desired 2-O-glyceryl-α-D-glucopyranoside also 1-O-glyceryl-α-D-glucopyranoside. Separation of these two products would be exceedingly difficult. It is also of particular importance that under the reaction conditions of the method of the present invention the formation of hydrolysis product is prevented efficiently such that more than 90%, preferably more than 95%, more preferably more than 98% of the glucosyl moiety of the converted donor is transferred into the desired product.

If, for instance, sucrose is used as glucosyl donor a product comprising natural αGG and fructose is obtained. If Glc 1-P is used as glucosyl donor a product comprising natural αGG and phosphate is obtained.

Therefore a product obtainable by the method of the present invention may further comprise fructose, preferably in an equimolar amount to αGG α-D-glucosylglycerol.

αGG is a naturally occurring molecule (a glycoside; a carbohydrate derivative) which serves the function of an osmoprotective substance and stabilizer in various microorganisms. Several publications have shown that isolated αGG has a range of outstanding properties which are of substantial interest for technological application. Uses of αGG and derivatives thereof include but are not limited to the fields of medicine (cancer therapy), cosmetics (moisturizing and stabilizing additive to a range of products), and food products (antidiabetics). Furthermore αGG is a very efficient stabilizer of biomolecules (proteins, lipids) and microorganisms.

Another aspect of the present invention relates to a cosmetic preparation comprising αGG according to the present invention.

The cosmetic products of the present invention are especially characterised by the fact that they only comprise natural αGG, which may be obtained by the method of the present invention.

Another aspect of the present invention relates to a pharmaceutical preparation comprising αGG according to the present invention.

Another aspect of the present invention relates to a food supplement comprising αGG or a product comprising αGG according to the present invention.

Another aspect of the present invention relates to the use of αGG or product comprising αGG according to the present invention as sweetener. A particular aspect is the use as sweetener of mixtures of αGG and fructose obtainable by the method of the present invention.

Another aspect of the present invention relates to the use of αGG as a stabilizing additive to preparations of biomolecules during storage or processing, in particular during drying. In particular, αGG can serve as a stabilizer of living microorganisms, proteins and lipid-derived structures. It can stabilize protein preparations, for example without being restricted thereto, antibodies, antibody fragments, and enzymes, against denaturation and loss of biological activity.

Another aspect of the present invention relates to the use of αGG as an additive that can facilitate protein folding, in particular that of recombinant proteins, under conditions in vitro as well as in vivo.

αGG may be in particular used as skin cleanser (JP 2004/331583), water-based cosmetic (JP 2004/331582), accumulation inhibitor of neutral fat (JP 2004/331580), production promoter of corium matrix (JP 2004/331579), cell activator (JP 2004/331578) and antibacterial agent (JP 2004/331577).

The present invention is further illustrated by the following figures and examples without being restricted thereto.

FIG. 1 shows the chemical structure of αGG.

Table 1 shows NMR data for αGG produced and purified according to the method of the present invention and demonstrate unequivocally the chemical structure in FIG. 1.

TABLE 1

NMR shift assignments in 2-O-glyceryl-α-D-glucopyranoside (αGG), measured directly from reaction mixture in $D_2O$ at 300K using external calibration with acetone (2.22 ppm $^1H$; 31.5 ppm $^{13}C$).

| Position | $^1H$ [ppm] | Mult | Koppl. [Hz] | Int | $^{13}C$ [ppm] |
|----------|-------------|------|-------------|-----|----------------|
| 1        | 5.21        | d    | 3.8         | 1H  | 98.2           |
| 2        | 3.66        | m    |             | 1H  | 72.4           |
| 3        | 3.84        | m    |             | 1H  | 73.3           |
| 4        | 3.52        | m    |             | 1H  | 69.9           |
| 5        | 3.93        | m    |             | 1H  | 71.9           |
| 6a       | 3.95        | m    |             | 1H  |                |
| 6b       | 3.83        | m    |             | 1H  | 61.0           |
| 1'a      | 3.80        | m    |             | 2H  |                |
| 1'b      | 3.75        | m    |             | 2H  | 63.8           |
| 2'       | 3.91        | m    |             | 1H  | 79.2           |

Suhr, R.; Scheel, O.; Thiem, J. *J. Carbohydr. Chem.* (1998) 17: 937-968

Figure 2:
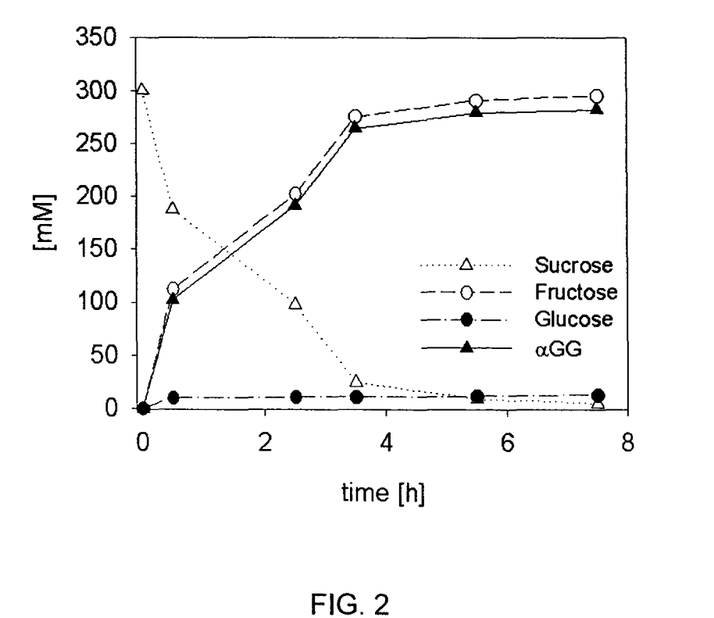
FIG. 2 is a plot that shows the production of αGG from sucrose and glycerol using free SPase from *Leuconostoc mesenteroides*.

FIG. 2 shows the production of αGG from sucrose and glycerol using free SPase from *Leuconostoc mesenteroides*. The enzymatic reaction was performed in a stirred batch system. A 50 mM MES buffer (pH 7) was used which contained 300 mM sucrose and 2 M glycerol as the substrates. The enzyme concentration was 20 IU/ml. In detail, the reaction mixture, containing 300 mM sucrose, 2 M glycerol and 20 IU/ml SPase in 50 mM MES buffer (pH 7), was incubated at 30° C. and 550 rpm for 7.5 hr. Under these optimum conditions selected, the yield of αGG was higher than 95%. The amount of released glucose was subtracted from the amount of released fructose to define the product.

Figure 3:
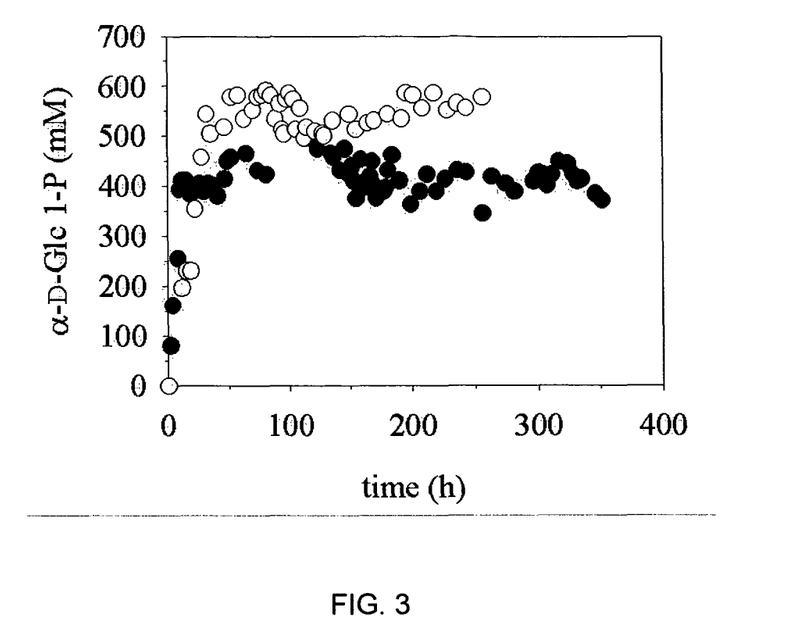
FIG. 3 is a plot that shows the operational stability of SPase from *Leuconostoc mesenteroides* immobilized on a polymer carrying oxirane groups.

FIG. 3 shows the operational stability of SPase from *Leuconostoc mesenteroides* immobilized on a polymer carrying oxirane groups. Results of continuous conversion of sucrose in a packed bed enzyme reactor are shown. The substrate solution contained 600 mM of each, sucrose and phosphate, in 20 mM MES buffer, pH 7.0. The reaction was carried out at 30° C. and a constant flow rate of 6 ml·h-1, corresponding to an average residence time of 8.8 h (53 ml, •) and 18.5 h (111 ml, ○), respectively.

Figure 4:
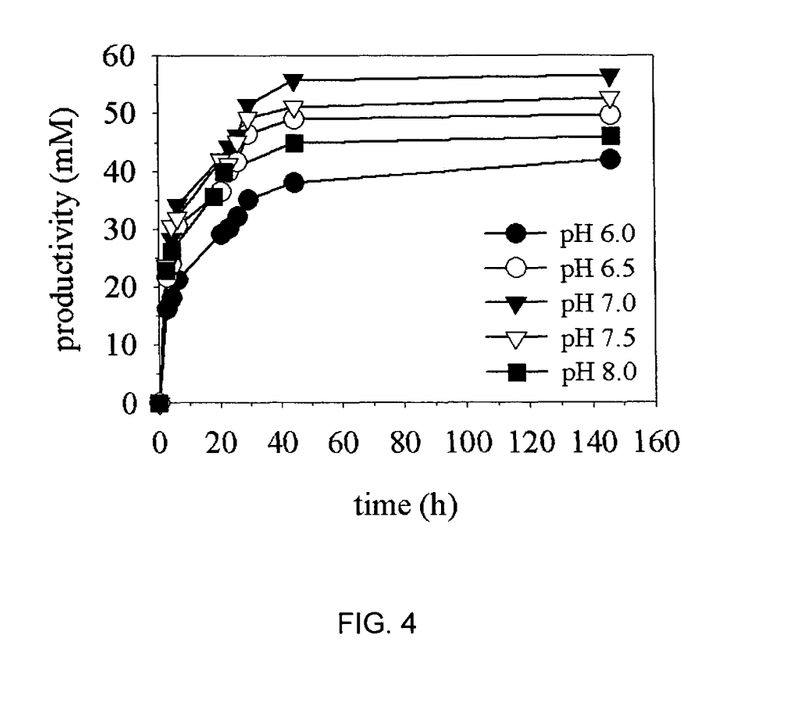
FIG. 4 is a plot that shows the synthesis of αGG by enzymatic glucosylation of glycerol using SPase from *Leuconostoc mesenteroides* at different pH values.

FIG. 4 shows the synthesis of αGG by enzymatic glucosylation of glycerol using SPase from *Leuconostoc mesenteroides* at different pH values. The reaction mixture contained 0.1 M Glc 1-P, 3 M glycerol and 3 IU/ml SPase in 40 mM MES buffer (pH 6.0, 6.5, 7.0) and 40 mM TES buffer (pH 7.5, 8.0), respectively. Conversions were performed at 30° C. and an agitation rate of 550 rpm. The amount of released glucose (cglc) was subtracted from the amount of released phosphate (cP) to define the productivity.

Figure 5:
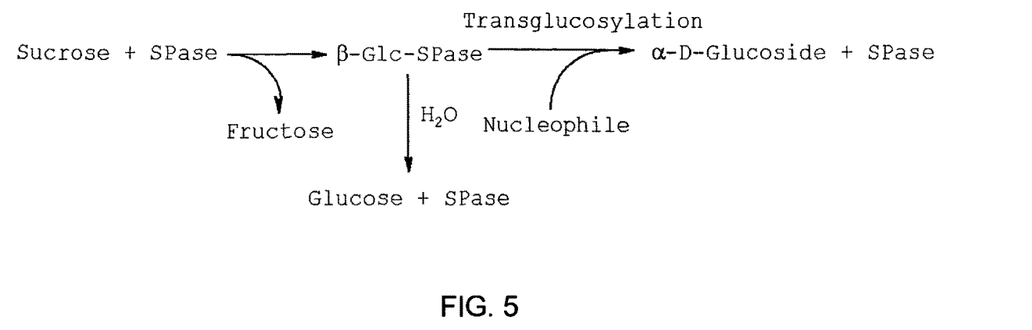
FIG. 5 is a schematic of the nucleophilic competition in the hydrolysis of sucrose by SPase leading to the synthesis of novel α-D-glucosides.

FIG. 5 shows the nucleophilic competition in the hydrolysis of sucrose by SPase leading to the synthesis of novel α-D-glucosides.

EXAMPLES

Example 1: Production of SPase

SPase can be obtained as a native enzyme or as a recombinant enzyme (for example but not restricted thereto, produced in *Escherichia coli*) according to reports in literature (Guibert A and Monsan P, Ann. N.Y. Acad. Sci. (1988) 504:307-311; Vandamme E J et al., Adv. Appl. Microbiol. (1987) 32:163-201; Kawasaki H et al., Biosci. Biotech. Biochem. (1996) 60:322-324; Kitao S and Nakano E, J. Ferment. Bioeng. (1992) 73:179-184; van den Broek L A M et al., Appl. Microbiol. Biotechnol. (2004) 65:219-227). It can of course be produced in various scales represented by shaken flask cultures of a suitable microorganism and bioreactors, preferably an aerated or nonaerated stirred tank reactor or a column reactor such as a bubble column or an airlift reactor. Partial purification or isolation of the enzyme is done using procedures described for SPase or by adopting general protocols of protein purification according to state of the art. Immobilization procedures such as, for example but not restricted thereto, covalent and noncovalent binding to insoluble carriers, encapsulation, and whole-cell systems, is done using protocols already developed for SPase or by adopting general protocols according to state of the art (Pimentel M C B and Ferreira M S S, Appl. Biochem. Biotechnol. (1991) 27:37-43; Soetaert W. et al., Progress in Biotechnology Vol. 10 (Petersen S. B., Svensson, B., Pederesen, S., Eds), Elsevier, Amsterdam; Vandamme E J et al., Adv. Appl. Microbiol. (1987) 32:163-201).

Example 2: Enzyme Assays

SPase activity was determined at 30° C. using a continuous coupled enzymatic assay, in which production of Glc 1-P from sucrose and inorganic phosphate is coupled to the reduction of $NAD^+$ in the presence of phosphoglucomutase (PGM) and glucose 6-phosphate dehydrogenase (G6P-DH). The standard assay was performed essentially as described elsewhere in 50 mM potassium phosphate buffer, pH 7.0, containing 10 mM EDTA, 10 mM $MgCl_2$ and 10 μM α-D-glucose 1,6-bisphosphate. The reaction mixture contained 250 mM sucrose, 2.5 mM $NAD^+$, 3 U·ml$^{-1}$ PGM, 3.4 U·ml$^{-1}$ $NAD^+$-dependent G6P-DH and the enzyme solution in appropriate dilution. The formation of NADH with time was monitored spectrophotometrically at 340 nm. One unit of SPase activity corresponds to the amount of enzyme that caused the reduction of 1 μmol of NAD+ per minute under the conditions described above. Protein concentrations were determined using the BioRad dye-binding method with bovine serum albumin as standard. Phosphate was determined colorimetrically at 850 nm and Glc 1-P was assayed in a coupled enzymatic system with PGM and G6P-DH.

Example 3: Immobilization of LmSPase onto a Polymer Containing Oxirane Groups

A total amount of 700 U of a preparation of crude SPase with a specific SPase activity of 50 U·mg$^{-1}$ was incubated at 4° C. with 10 g of Eupergit C in 0.7 M potassium phosphate buffer, pH 7.0, for 14 h. The agitation rate was 250 rpm. The immobilisate was washed several times with 20 mM MES buffer, pH 7.0. The binding efficiency, given by the ratio of the residual activity measured in the supernatant after the immobilisation and the total activity employed (U), was 0.5.

Example 4: Operational Stability of Immobilized SPase

Eupergit C, onto which SPase was attached, was packed in a GE Healthcare XK26/40 glass column (2.6 cm; 53 ml or 111 ml, 34 $U \cdot g^{-1}$ Eupergit C), equipped with a thermostatic jacket. The column was equilibrated with 20 mM MES buffer, pH 7.0. The substrate solution contained 600 mM of each, sucrose and phosphate in the same buffer, and was brought to reaction temperature (30° C.) by incubation in a water bath. The solution was pumped through the packed bed at a constant flow rate of 6 $ml \cdot h^{-1}$ delivered from a GE Healthcare piston pump (model P500). The temperature at the outlet of the reactor was monitored continuously. At certain times, 1-ml samples were taken and used for further analysis.

FIG. 3 shows the time course of Glc 1-P production in a continuous fixed bed reactor operated at a constant axial flow rate of 1.13 $cm \cdot h^{-1}$. Depending on the average residence time determined by the bed height, 8.8 h or 18.5 h, the conversion of sucrose (600 mM) was 68% and 91% respectively. The corresponding productivities, calculated as $g \cdot l^{-1}$ product×reciprocal residence time, were 15.4 $g \cdot (l \cdot h)^{-1}$ and 10.9 $g \cdot (l \cdot h)^{-1}$. Note that the conversion rate remained constant up to extended reaction times of 650 h, emphasising the excellent stability of immobilised SPase under the operational conditions.

Example 5: Synthesis of αGG Using Glc 1-P as the Donor

The reaction mixture contained 0.1 M Glc 1-P, 3 M glycerol and 3 $IU \cdot ml^{-1}$ LmSPase in 40 mM MES buffer (pH 6.0, 6.5, 7.0) or 40 mM TES buffer (pH 7.5, 8.0). The enzymatic conversion was followed over time at 30° C. and an agitation rate of 550 rpm. The concentrations of released phosphate (cP) and glucose (cglc) were determined. The amount of transglucosylation product formed corresponds to cP—cglc. Results are shown in FIG. 4.

Example 6: Synthesis of αGG Using Sucrose as the Donor

The reaction mixture, containing 300 mM sucrose, 2 M glycerol and 20 U/ml SPase in 50 mM MES buffer (pH 7), was incubated at 30° C. and 550 rpm for 7.5 hr. Under these optimum conditions selected, the yield of αGG was higher than 95% (FIG. 2). Product analysis was done using HPLC employing a BioRad HPX-87C column and reflection index detection. The column was kept at 85° C. and deionized water was used as eluent at a flow rate of 0.6 ml/min. The amount of released glucose was measured using state-of-the-art glucose oxidase/peroxidase assay. NMR analyses, shown in Table 1, confirmed the correct structure of αGG and the composition of the product mixture. Note that hydrolysis (i.e. formation of glucose) is prevented efficiently under the conditions used in Examples 10a and 10b.

Example 7: Purification of αGG

About 90 ml of product, obtained as in example 6 except that 800 mM sucrose was used, were loaded onto a column (XK 50/60, GE Healtcare) packed with about 1 litre of a 1:1 mixture of activated charcoal Norit® (Type Norit SX Ultra) and Celite® 501 (Filter Aid, calcined). The column was equilibrated with water. The product solution contained 16.3 g αGG, 12.4 g fructose, 2.2 g sucrose, 13.1 g glycerol and 0.8 g glucose. Elution was performed using a step-gradient of ethanol in water, using 4 litres of water, followed by 4 litres of 2% ethanol, and finally 2 litres of 15% ethanol. αGG elutes at 2% ethanol, separated from unreacted sucrose as well as fructose. Glycerol is present in the water fraction. The yield of recovered αGG is 56%, and the purity of αGG assessed by HPLC is greater than 98%.

Example 8: Stabilization of Proteins During Freeze Drying

The protein of interest (e.g. mannitol dehydrogenase, MDH) was incubated at a concentration of 0.8 mg/ml in the presence of 0, 20, 50, 100, 500, 1000 or 1500 mM αGG in 100 mM Tris/HCl buffer, pH 7.0. The samples were lyophilized over-night and dissolved in the same buffer again. The specific enzyme activity was determined, using appropriate assays for the corresponding enzyme as described elsewhere (Slatner M. et al., Biochemistry 38: 10489-10498), before and after freeze drying. Without any stabilizer added the enzymatic activity of MDH dropped down to 2% after freeze drying, whereas αGG is able to maintain enzymatic activity up to 48% irrespective of the added αGG concentration.

The invention claimed is:

1. A method of stabilizing biomolecules comprising making a α-D-glucosylglycerol (αGG) by the steps of:
   providing a sucrose phosphorylase (EC 2.4.1.7);
   incubating said sucrose phosphorylase with a mixture comprising sucrose and glycerol; and
   at least one of isolating or purifying α-D-glucosylglycerol from said mixture; and
   mixing said α-D-glucosylglycerol with one or more biomolecules to stabilize the one or more biomolecules, wherein the biomolecules are selected from proteins, and protein fragments and lipid-derived structures during processing and storage.

2. A method of preparing a cosmetic composition comprising
   preparing a α-D-glucosylglycerol (αGG) by the steps of:
   providing a sucrose phosphorylase (EC 2.4.1.7);
   incubating said sucrose phosphorylase with a mixture comprising sucrose and glycerol; and
   at least one of isolating or purifying α-D-glucosylglycerol from said mixture;
   providing a cosmetically acceptable carrier; and mixing said α-D-glucosylglycerol and said carrier.

3. The method of claim 1, wherein the α-D-glucosylglycerol or product comprising α-D-glucosylglycerol at least one of: assists protein refolding from inclusion bodies, prevents protein misfolding, or prevents protein aggregation in vivo.

4. The method of claim 1, wherein the α-D-glucosylglycerol or product comprising α-D-glucosylglycerol improves cell viability during recombinant protein production.

5. The method of claim 1, wherein the α-D-glucosylglycerol or product comprising α-D-glucosylglycerol improves the stability of enzymes under reaction conditions.

6. The method of claim 1, wherein during the steps of isolating, purifying, or both, the α-D-glucosylglycerol is obtained in a purity of greater than 80%.

7. The method according to claim 1, wherein the sucrose phosphorylase is from *Agrobacterium vitis* (NCBI P33910), *Bifidobacterium adolescentis* (Q84HQ2), *Bifidobacterium longum* (Q84BY1), *Escherichia coli* (P76041), *Escherichia coli* 06 (Q8FHS2), *Lactobacillus acidophilus* (Q7WWP8, Q7WWQ5), *Lactobacillus delbrueckii* subsp. *lactis* (Q71I99), *Leuconostoc mesenteroides* (Q59495, Q9R5Q3), *Listeria monocytogenes* (Q4ENE7, Q4EQR2, Q4ETN7, Q4EHA0, Q4EJW2, Q4ELY7), *Pseudomonas putrefaciens*, *Pseudomonas saccharophila* (AAD40317), *Rhodopirellula baltica* (Q7UIS9), *Shewanella baltica* (Q3Q4P1), *Shewanella frigidimarina* (Q3NMD1), *Solibacter usitatus* (Q43TL5), *Streptococcus mutans* (P10249) and/or *Synechococcus* sp. (068858, Q7U3J7).

8. The method according to claim 1, further comprising the step of immobilizing the sucrose phosphorylase on a carrier.

9. The method according to claim 8, wherein said carrier is a solid support.

10. The method according to claim 9, wherein the carrier is a chromatography resin, an anion exchange chromatography resin, a cation exchange chromatography resin, an affinity chromatography resin or a hydrophobic interaction chromatography resin.

11. The method according to claim 1, wherein the incubation is performed at a pH value of 4 to 10.

12. The method according to claim 1, wherein the incubation is performed for at least 15 min.

13. The method according to claim 1, wherein the incubation is performed at a temperature range of 10 to 50° C.

14. The method according to claim 1, wherein the mixture comprises the glucosyl donor in a concentration of 0.01 to 3 mol/l.

15. The method according to claim 1, wherein the mixture comprises glycerol in a concentration of 0.01 to 10 mol/l.

16. The method of claim 1, wherein the sample comprises one or more living microorganisms during processing and storage.

17. The method of claim 1, wherein the proteins are dried or lyophilized.

18. The method of claim 1, wherein the sample comprises *Escherichia coli*.

19. The method of claim 2, wherein the composition is formulated to treat cancer.

20. A method of enhancing protein stability in a cosmetic comprising:
providing α-D-glucosylglycerol (αGG) obtainable by the steps of:
providing a sucrose phosphorylase (EC 2.4.1.7);
incubating said sucrose phosphorylase with a mixture comprising sucrose and glycerol; and
at least one of isolating or purifying α-D-glucosylglycerol from said mixture; and
mixing said α-D-glucosylglycerol with the cosmetic sample comprising proteins in need of enhanced stability, wherein the α-D-glucosylglycerol at least one of: increases protein refolding in inclusion bodies, prevents protein misfolding, prevents protein aggregation in vivo, improves cell viability during recombinant protein production, or improves the stability of protein enzymes under reaction conditions.

21. The method of claim 20, wherein the α-D-glucosylglycerol is added as a moisturizing and stabilizing additive to the cosmetic.

* * * * *